United States Patent
Kim et al.

(10) Patent No.: US 7,361,371 B2
(45) Date of Patent: Apr. 22, 2008

(54) **EXTRACT OF *PETASITES JAPONICUS* HAVING NEUROPROTECTIVE EFFECT AND ANTIOXIDANT ACTIVITY**

(75) Inventors: Mee Ree Kim, Daejeon (KR); Dai-Eun Sok, Daejeon (KR); Sang-Hee Oh, Daejeon (KR); Yun-Bae Kim, Daejeon (KR)

(73) Assignee: Industry & Acacemic Cooreration in Chungnam National University (IAC) (KR)

( * ) Notice: Subject to any disclaimer, the term of this patent is extended or adjusted under 35 U.S.C. 154(b) by 138 days.

(21) Appl. No.: 10/548,935

(22) PCT Filed: Mar. 15, 2004

(86) PCT No.: PCT/KR2004/000543

§ 371 (c)(1),
(2), (4) Date: Sep. 12, 2005

(87) PCT Pub. No.: WO2004/080473

PCT Pub. Date: Sep. 23, 2004

(65) Prior Publication Data

US 2006/0210652 A1 Sep. 21, 2006

(30) Foreign Application Priority Data

Mar. 14, 2003 (KR) .................. 10-2003-0016137

(51) Int. Cl.
*A61K 36/00* (2006.01)
(52) U.S. Cl. .................................... 424/725
(58) Field of Classification Search ............ None
See application file for complete search history.

(56) References Cited

U.S. PATENT DOCUMENTS

| | | | |
|---|---|---|---|
| 6,770,263 B1 * | 8/2004 | Brucker | 424/45 |
| 7,090,871 B2 * | 8/2006 | Koch et al. | 424/725 |
| 2004/0161524 A1 * | 8/2004 | Sakai et al. | 426/655 |
| 2004/0224039 A1 * | 11/2004 | Brucker | 424/771 |

(Continued)

FOREIGN PATENT DOCUMENTS

KR 1020030011464 A 2/2003

(Continued)

OTHER PUBLICATIONS

Matsuura et al, Isolation and Measurement of Quercetin Glucosides in Flower Buds of Japanese Butterbur (*Petasites japonicus* subsp. *gigantea* Kitam., Biosci. Biotechnol. Biochem, vol. 66, No. (7), 2002, pp. 1571-1575.*

(Continued)

*Primary Examiner*—Christopher R. Tate
*Assistant Examiner*—Deborah A. Davis
(74) *Attorney, Agent, or Firm*—Cantor Colburn LLP (57) ABSTRACT

The present invention relates to an extract of *Petasites japonicus* having antioxidant activity, and more particularly, to an extract of *Petasites japonicus* having antioxidant activity which is extracted using an alcohol and an antioxidant for the prevention and treatment of a brain disease comprising the extract as an effective ingredient. The *Petasites japonicus* extract according to the present invention has excellent antioxidant activity, relief of neurotoxicity and neuroprotective effect and thus, can be usefully used in the prevention and treatment of brain diseases such as Alzheimer's disease, Parkinson's disease, amyotrophic lateral sclerosis, hypoxic-ischemic injury and chronic spinal cord injury.

5 Claims, 4 Drawing Sheets

U.S. PATENT DOCUMENTS

2006/0228426 A1* 10/2006 Cyr ........................... 424/725

FOREIGN PATENT DOCUMENTS

KR          1020030039726 A       5/2003

OTHER PUBLICATIONS

"Immunohistochemical Study of Advanced Glycation End Products in Aging and Alzheimer's Disease Brain"; Authors: Akinori Takeda, Takeshi Yasuda, Toshio Miyata, Keiko Mizuno, Mei Li, Sakae Yoneyama, Katsunori Horie, Kenji Maeda, Gen Sobue; Elsevier Science Ireland Ltd., Neuroscience Letters 221 (1996); pp. 17-20.
"Bioenergetic and Oxidative Stress in Neurodegenerative Diseases"; Authors: Allen C. Bowling and M. Flint Beal; Life Sciences, vol. 56, No. 14, pp. 1151-1171, 1995.
"Excitatory Amino Acid Release and Free Radical Formation May Cooperate in the Genesis of Ischemia-Induced Neuronal Damage"; Authors: Domenica E. Pellegrini-Giampietro, Giovanna Cherici, Marina Alesiani, Vincenzo Carla, and Flavio Moroni; The Journal of Neuroscience, Mar. 1990, 10 (3); pp. 1035-1041.
"Oxidative Stress, Glutamate, and Neurodegenerative Disorders"; Authors: Joseph T. Coyle and Pamela Puttfarcken; Science, vol. 262, Oct. 29, 1993; pp. 689-695.
"An Enzymic Function for Erythrocuprein (Hemocuprein)", The Journal of Biological Chemistry, vol. 244, No. 22, Jun. 23, 1969; pp. 6049-6055.
"Melatonin Maintains Glutathione Homeostasis in Kainic Acid-Exposed Rat Brain Tissues"; Authors: Maura Floreani, Stephen D. Skaper, Laura CFacci, Maria Lipartiti, and Pietro Glustl; The FASEB Journal; vol. 11, Dec. 1997, pp. 1309-1315.
"Chemical and Molecular Regulationof Enzymes That Detoxify Carcinogens"; Proc. Natl. Acad. Sci. USA, vol. 90; Apr. 1993; pp. 2965-2969.
"Antimutagenic Effect of Flavonoids Isolated From Oenanthe Javanica"; J. Korean Soc. Food Sci. Nutr., 25 (4) 19996; pp. 588-592.
Induction of Hepatic Glutathione S-Transferase Activity in Mice Administered Iwth Vrius Vegetable Extracts; Authors: Mee Ree Kim, Kun-Jong Lee, Yun-Bae Kim and Dai-Eun Sok; J. Food Sci. Nutr., vol. 2, No. 3 (1997), pp. 207-213.
"Effect of Various Kimchi Extracts on the Hepatic Glutathione S-Transferase Activity of Mice"; Authors: Mee Ree Kim, Kun-Jong Lee, Hee Young Kim, Jin Hee Kim, Yun-Bae Kim and Dai-Eun Sok, Food Research Int'l., vol. 31, No. 5 (1999), pp. 389-394.
"Effects of Placing Micro-Implants of Melatonin in Striatum on Oxidative Streee and Neuronal Damage Medicated by N-Methyl-D-Asparate (NMDA) and Non-NMDA Receptors"; Authors: Hwa-Jung Kim and Jin Suk Kwon; Afch Pharm Res vol. 22, No. 1, (1999), pp. 35-43.
"Petasins in the Treatment of Allergic Diseases: Results of Preclinical and clinical studies"; Authors: O.A.R. Thomet; H.-U. Simon; Int Arch Allergy Immunol, 2002, 129(2), 108-12.
"Mutations in Cu/Zn superoxide dismutase are associated with familial amyotrophic lateral sclerosis"; Authors: Daniel R. Rosen, et al.; Letters to Nature, vol. 362, pp. 59-62 (1993).
J. Neurochem., vol. 69, p. S19 (1997).
"Free Radicals in Biology and Medicine" Authors: Barry Halliwell and John M. C. Gutteridge; Clarendon Press, Oxford, 2nd Edition (1989).
"Kainic acid: a powerful neurotoxic analogue of glutamate"; Authors: John W. Olney, Vesela Rhee, and Oi Lan Ho; Brain Research, 77, pp. 507-512 (1974).
"Kainic Acid Seizures in the Rat"; Author: Gunther Sperk; Progress Neurobiology, vol. 42, pp. 1-32 (1994).
The Importance of Sample Preparation and Storage in Glutathione Analysis; Authors: Jeanette C. Roberts and David J. Francetic; Analytical Biochemistry 211, pp. 183-187 (1993).
"Dietary Polyunsaturated Fatty Acids and Aging Modulate Glutathione- Related Antioxidants in Rat Liver"; Authors: Raymond Christon, Rahma Belcadi Haloui, and Georges Durand; J. Nutr. 125, pp. 3062-3070, (1995).
"Depletion of cytosolic GSH decreases the ATP levels and viability of synaptosomes from aged mice but not from young mice"; Authors: Marcos Martinez, et al.; Mechanisms of Aging and Development 84, pp. 77-81, (1995).
Relative Susceptibility of Microsomes from Lung, Heart, Liver, Kidney, Brain, andTestes to Lipid Peroxidation: Correlation with Vitamin E Content; Authors: Douglas J. Kornbrust and Richard D. Mavis; LIPIDS, vol. 15, No. 5, pp. 315-322, (1980).
"Vitamin E and Selenium Protection from In Vivo Lipid Peroxidation"; Author: Al L. Tappel; Annals New York Academy of Sciences, 335, pp. 18-31, (1982).
"Vitamin E Dependant Reduced Glutathione Inhibition of Rat Liver Microsomal Lipid Peroxidation"; Authors: C. Channa Reddy, Richard W. Scholz, Craig E. Thomas, and Edward J. Massaro; Life Sciences, vol. 31, pp. 571-576, (1982).
"Microsomal Electron Transport"; Authors: Lars Ernster and Kerstin Nordenbrand; Methods of Enzymology, vol. 10, pp. 574-580, (1975).
"Inhibitory Effect of Sodium Ascorbate on Ethylurea and Sodium Nitrite Carcinogensis and Negative Findings in Progeny After Intestinal Inoculation of Precursors Into Pregnant Hamsters"; Author: Mario Rustia; Journal of the National Cancer Institute, vol. 55, No. 6, pp. 1389-1393; (1975).
Biochemical function of selenium and its relation to vitamin E; Author: William G. Hoekstra; Federation Proceedings, vol. 34, No. 11, pp. 2083-2089, (1975).
"Glutathione Peroxidase and Hydroperoxides"; Author: Al L. Tapper; Methods of Enzymology, 52, pp. 506-523, (1978).
"Rat Hepatic Cytosolic Glutathione- Dependent Enzyme Protection Against Lipid Peroxidation in the NADPH- Microsomal Lipid Peroxidation System"; Authors: Raymond F. Burk, et al; Biochem. Biophys. Acta., 618, pp. 35-41, (1980).
"Enzymic Method for Quantitative Determination of Nanogram Amounts of Total and Oxidized Glutathione: Applications to Mammalian Blood and Other Tissues"; Author: Frank Tietze; Analytical Biochemistry 27, pp. 502-522, (1969).
"A "Radical" View of Cerebral Ischemic Injury"; Author: John W. Phillis; Progress in Neurobiology, vol. 42, pp. 441-448, (1994).
"NMDA Antagonist Neurotoxicity Mechanism and Prevention"; Authors: J.W. Olney, et al.; SCIENCE, vol. 254, pp. 1515-1518, (1991).
"NMDA antagonists partially protect against MPTP induced neurotoxicity in mice"; Authors: Emmanuel Brouillet and M. Flint Beal; NeuroReport 4, pp. 387-390, (1993).
"Petasites hybridus: Ancient Medicinal Plant is Effective Prophylactic Treatment for Migraine"; Author: Alexander Mausko; Townsend Letter for Doctors and Patients, pp. 104 & 106, (2000).
"Protective effect of vegetable extracts on oxidative stress in brain of mice administered with NMDA"; Authors: Kun-Jong Lee, et al.; Food Research International, 35, pp. 55-63, (2002).
Hui Song Cui, Mee Ree Kim, Dai-Eun Sok, Protection by Petaslignolide A, a Major Neuroprotective Compound in the Butanol Extract of *Petasites japonicus* Leaves, against Oxidative Damage in the Brains of Mice Challenged with Kainic Acid, J. Agric. Food Chem. 53(22),8526, 2005.
Min BS, Cui HS, Lee HK, Sok DE, Kim MR, A New Furofuran Lignan with Antioxidant and Anti-Seizure Activities from the Leaves of *Petasites japonicus,* Arch. Pharm. Res. Sep. 2005;28(9):1023.
Dajas F, Rivera-Megret F, Blasina F, Arredondo F, Abin-Carriquiry JA, Costa G, Echverry C, Lafon L, Heizen H, Ferreira M, Morquio A. "Neuroprotection by flavonoids", Braz. J. Med. Biol. Res. Dec. 2003;36(12):1613.

* cited by examiner

EXTRACT OF *PETASITES JAPONICUS* HAVING NEUROPROTECTIVE EFFECT AND ANTIOXIDANT ACTIVITY

TECHNICAL FIELD

The present invention relates to an extract of *Petasites japonicus* and an antioxidant for preventing and treating a brain disease comprising the same.

BACKGROUND ART

Recently, as the standard of living is elevated, the average span of human beings' lives is lengthened and the importance of the aged people is increased. Upon examining the cause of death of Korean people, brain diseases such as stroke, dementia, mental disorders and behavior disorders occupy the high rank of death cause, following cancers and diseases of the circulatory system, and rank the top among single organ diseases (Korean Statistics Yearbook, death toll according to sex, age and death cause, 1996). Representative brain diseases include Alzheimer's disease (AD) (Furuta, A. et al., *Am. J. Pathol.*, 1995, 146, 357-367; Good, D. F. et al., *Am. J. Pathol.*, 1996, 149(1), 21-28), multiple sclerosis (MS) (Takeda, A. et al., *Neuroscience letters*, 1996, 21, 17-20), Lou Gehrig's disease (amyotrophic lateral sclerosis: ALS) (Rosen. D. R. et al., *Nature*, 1993, 362, 59-62), Parkinson's disease (PD) (Bowling, A. C. and Beal, M. F., *Life Sci.*, 1995, 56(14), 1151-1171), stroke, ischemia and the like. Particularly, in case of senile brain diseases including Alzheimer's disease, Parkinson's disease and stroke, oxidative stress accompanying the formation of a radical in a cerebral cell is one of the important etiological factors (Smith, M. A., *J. Neurochem.*, 1997, Supp. Sl, 69, 19).

The oxidative stress means damage of cells or tissues by toxic free radicals and it is known that neuronal damage by the oxidative stress is involved in damage of brain cells which occurs during normal aging and neurodegenerative disease such as Alzheimer's disease, Parkinson's disease, amyotrophic lateral sclerosis, dementia and the like (Good, D. F. et al., *Am. J. Pathol.*, 1996, 149(1), 21-28; Bowling, A. C. and Beal, M. F., *Life Sci.*, 1995, 56(14), 1151-1171; Smith, M. A., *J. Neurochem.*, 69, 1997, Supp. Sl, 19). In the brain tissues, a large quantity of oxygen is consumed to produce ATP by oxidizing sugar. Generally, an adult consumes 3.5 ml of oxygen per minute for 100 g of brain tissue. Though the brain weight is only 2% of the body weight, the oxygen consumption is 20% of the total and thus, the partial pressure of oxygen in the brain is great. As the partial pressure of oxygen in the brain is increased, activity of glutamate decarboxylase is reduced or the oxygen free radical formation is increased, inducing convulsion (Halliwell, B., and Gutteridge, J. M. C., *Free Radicals in Biology and Medicine*, 1989, 2nd Ed, Clarendon Press, Oxford). Particularly, the brain tissue is known to be susceptible of free radical attack since the cerebral cells do not have sufficient defense mechanisms and contains a high concentration of long chain unsaturated fatty acids which are liable to be oxidized and metal ions ($Fe^{2+}$, $Cu^{2+}$) which are used as a catalyst upon radical formation.

In the nervous system of mammals, over-excitation of the excitatory amino acids system (EAAs system) induces diseases such as epilepsy, Alzheimer's disease, Parkinson's disease, stroke, metal diseases (trauma) and the like, in which oxidative stress caused by increase of free radicals takes part in the induction of such diseases (Rosen. D. R. et al., *Nature*, 1993, 362, 59-62; Pellegrini-Giampietro, D. E. et al., *J. Neurosci*, 1990, 10, 1035-1041). Substances activating the excitatory amino acids system to cause brain damage is called as excitotoxins and the excitatory amino acids system overexcited by the excitotoxins induces introduction of ions into nerve cells and free radical production, causing damage of the nerve cells. Glutamate receptor in the excitatory amino acids system is a kind of a ligand-gated ion channel and is classified into NMDA (N-methyl-D-aspartate), AMPA (α-amino-4-isoxazole-propionic acid), kainic acid (KA) receptor according to antagonist selectivity. Overstimulation of these receptors causes damage of nerve cells. When NMDA receptor is over-stimulated, lipid, protein and nucleic acid which are components of a cell are decomposed due to the introduction of $Ca^{2+}$ while when non-NMDA receptors are over-stimulated, $Na^+$ is introduced, causing swelling of nerve cells. Also, when kainic acid, a non-NMDA receptor, is activated, damage of nerve cells is induced by the production of a large quantity of reactive oxygen species (hereinafter referred to as "ROS") (Olney, J. W. et al., *Brain Res*, 1974, 77, 507-512). The kainic acid which is a strong excitotoxin in the central nerve system shows acute or subacute epileptiform activity lasting for several hours or several days and ultimately causes irreversible neuropathological change in glia, myelin sheaths and the like as well as nerve-cells (Sperk, G., *Prog. Neurobiol*, 1994, 42, 1-32). In addition, the kainic acid directly induces brain damage and releases glutamate in an amount to show cerebral toxicity (Roberts, J. C. and Francetic, D. J., *Anal. Biochem*, 1993, 211, 183-187). The kainic acid-induced neuronal death results from destruction of cell membrane caused by production of ROS and such neurotoxicity is prevented by administration of an antioxidant (Coyle, J. T., and Puttfarcken, P. *Science*, 1993, 262, 689-695).

In recent, researches for substances selectively inducing oxidative stress in the brain have been actively conducted and also researches for protective agent against oxidative stress are actively conducted. Protective agents against ROS existing in cells include glutathione (Roberts, J. C. and Francetic, D. *J. Anal. Biochem*, 1993, 211, 183-187; Raymond C. et al., *J. Nutr.*, 1995, 125, 3062-3070; Marcos M. et al., *J. Mechanisms of ageing and development*, 1995, 84, 77-81), α-tocopherol (Hoekstra, W. G., *Fed. Proc.*, 1975, 34, 2083-2089; Kormbrist, D. J. and Movis, R. D., *Lipids*, 1980, 15, 315-322; Tappel, A. L., Ann. N.Y. *Acad. Sci.*, 1980, 355, 18-31; Reddy C. C. et al., *Life Sci.*, 1982, 31, 571-576), vitamin A (Ernster, L. and Nordenbrand, K., *Methods in Enzymology*, 1967, 10, 574-580), vitamin C (Rustia, M., *J. Natl. Cancer Inst.*, 1975, 55, 1389-1393), selenium (Hoekstra, W. G. *Fed. Proc.*, 1975, 34, 2083-2089) and the like, and antioxidant enzymes include SOD (McCord and Fridovich, *J. Biol. Chem.*, 1969, 224, 6049-6055), catalase, glutathione peroxidase (Roberts, J. C. and Francetic, D. J., *Anal. Biochem.*, 1993, 211, 183-187; Tappel, A. L. *Methods in Enzymology*, 1978, 52, 506-523), glutathione S-transferase (Roberts, J. C. and Francetic, D. J., *Anal. Biochem.*, 1993, 211, 183-187; Burk, R. F. et al., *Biochem. Biophys. Acta.*, 1980, 618, 35-41), glutathione reductase (Tietze, F., *Anal. Biochem.*, 1969, 27, 502-522; Floreani M, et al., *FASEB J.*, 1997, 11, 1309-1315; Phillis, J. W., *Prog. Neurobiol.*, 1994, 42, 441-448), quinone reductase (Prestera, T. et al., *Proc. Natl. Acad. Sci. USA*, 1993, 90, 2969) and the like.

Up to date, there have been reported effects of various natural antioxidants for antioxidant protection against oxygen radical produced in cells, which are mainly related to antioxidant functions of herbs or food ingredients in liver tissue, while giving a poor showing in connection with antioxidation in brain tissue (Park, J. C. et al., *J. Korean Soc. Food Nutr.*, 1996, 25, 588-592; Kim, M. R. et al., *J. Food. Sci. Nutr.*, 1997, 2, 207; Kim, Mee Ree, et al., *Food Res. Intl.*, 1999, 31(5), 389-394). Meanwhile, researches for development of a treating agent to prevent senile brain diseases are focused on neuroprotective treatment. In recent, scavengers of free radicals, calcium antagonists, NMDA and non-NMDA receptor antagonists and the like have been developed and partially used. However they are not yet proved to be stable in the human body as an antioxidant for brain protection (Olney, J. W. et al., *Science*, 1991, 254, 1515-1518; Brouillet, E. and Beal M. F., *NeuroReport.*, 1993, 4, 387-390; Kim, W. J. Kwon, J. S., *Arch. Pharm. Res.*, 1999, 22, 35-43). From this point of view, edible plant resources which we commonly eat are verified for their stability in the human body to some degree. However, researches are mainly focused on their antioxidant effects in the liver tissue and research aiming at brain protection is insufficient.

Butterbur (common name: Butterbur or scientific name: *Petasites japonicus*) is a perennial shrub found in a part of Asia and North America as well as Europe. Extract extracted from the roots and leaves of butterbur has been used as a therapeutic substance for more than 2,000 years. At the present time, the extract of *Petasites japonicus* is commonly used to relax muscles, treated in the conditions such as abdominal pain in the stomach and intestines, convulsion of a smooth muscle, shows pain relief effect and may be used for headache (Eaton J., *Townsend Lett*, 2000, 202, 104-106). Also, it has been reported that *Petasites japonicus* has therapeutic effects on asthma and allergic diseases (Thomet OA, Simon HU, *Int Arch Allergy Immunol*, 2002, 129(2), 108-12). However, there has not yet been shown that *Petasites japonicus* has antioxidant effect. Thus, the present inventors have investigated plant resources having antioxidant activity to prepare a therapeutic and prophylactic agent of brain diseases and found that *Petasites japonicus* extract shows excellent antioxidant activity. Based on the above discovery, the present invention has been completed.

DISCLOSURE OF INVENTION

Therefore, it is an object of the present invention to provide extract of *Petasites japonicus* having antioxidant activity and an antioxidant for prevention and treatment of brain diseases comprising the same.

In order to achieve the above object, the present invention provides an extract of *Petasites japonicus* having antioxidant activity which is produced by extracting *Petasites japonicus* with water, an alcohol or a mixture of water and an alcohol.

Also, the present invention provides an antioxidant for prevention and treatment of brain diseases comprising the extract of *Petasites japonicus* as an effective ingredient.

Now, the present invention will be described in detail.

The present invention is directed to an extract of *Petasites japonicus* having antioxidant activity which is obtainable by extracting *Petasites japonicus* with water, an alcohol or a mixture of water and an alcohol.

The extract of *Petasites japonicus* having antioxidant activity according to the present invention is produced by a method comprising the steps of:

1) extracting and concentrating *Petasites japonicus* with an alcohol to obtain an alcohol extract;

2) fractionating the alcohol extract from the step 1) with hexane and water into a hexane phase and a water phase and separating the water phase; and 3) fractionating the water phase from the step 2) with chloroform into a chloroform phase and a water phase and separating the water phase.

Also, the extract according to the present invention is produced by further subjecting the extract of *Petasites japonicus* obtained from the above-described method to the steps of:

1) fractionating the extract of *Petasites japonicus* with ethyl acetate into an ethyl acetate phase and a water phase and separating the water phase;

2) fractionating the water phase from the step 1) with butanol into an butanol phase and a water phase and separating the butanol phase; and 3) vaporizing the butanol phase from the step 2) at a low temperature and a low pressure to purify the butanol phase, or adding butanol to the butanol phase from the step 2) to obtain a soluble phase.

The alcohol is preferably methanol or ethanol, with methanol being more preferable. Also, the methanol is preferably 95 to 100% and the extraction is preferably performed 3 to 4 times in a dark room at 15 to 20° C. In a preferred embodiment according to the present invention, ground and dried *Petasites japonicus* was treated with 99.9% methanol and extracted three times in a dark room at 15° C.

Also, as seen from preferred embodiments according to the present invention, in the experiment examining antioxidant activity of fractions obtained by extracting the methanol extract of *Petasites japonicus* with various solvents, the ethyl acetate fraction and the butanol fraction of *Petasites japonicus* show excellent antioxidant activity (See Table 1). Also, when the butanol fraction of *Petasites japonicus* is directly administered to mice, it is shown that kainic acid (KA)-induced fatality rate is reduced (See Table 2 and Table 3) no side effects is observed with no change in body weight and brain weight (See Table 4 and Table 5), and neurotoxic behavior induced by KA is relieved (Table 6). Also, it is noted that the extract of *Petasites japonicus* has inhibiting effect on damage of cerebral nerve cells (FIG. 2, FIG. 3a and FIG. 3b) and the extract of *Petasites japonicus* is able to relieve neurotoxicity and protect nerve cells. Further, it is noted that the extract of *Petasites japonicus* according to the present invention recovers the reduction in production of glutathione induced by KA to a normal level (FIG. 4), prevents KA-induced lipid peroxidation (FIG. 5), and recovers antioxidant enzyme activity which has been reduced by KA to a normal level (FIG. 6a). Therefore, it is proved that the extract of *Petasites japonicus* has excellent antioxidant activity.

Accordingly, the extract of *Petasites japonicus* according to the present invention is obtained through a methanol extraction step. Preferably, the extract is further subjected to an ethyl acetate extraction step and more preferably, further subjected to a butanol extraction step. Also, after the butanol extraction step, the extract is re-extracted with butanol.

Also, the present invention provides an antioxidant for prevention and treatment of a brain disease comprising the extract of *Petasites japonicus* as an effective ingredient.

The *Petasites japonicus* extract according to the present invention has excellent neuroprotective effect and antioxidant activity and thus, may be usefully used in the prevention and treatment of a brain disease induced by oxidative stress, that is, peroxidation.

The brain disease which can be prevented and treated by using the extract according to the present invention is preferably selected from the group consisting of Alzheimer's disease, Parkinson's disease, amyotrophic lateral sclerosis, hypoxic-ischemic injury and chronic spinal cord injury, of which a main pathological factor is oxidative stress. However, the disease is not particularly limited to the above-described diseases but is applicable to any brain diseases as long as they are induced by oxidative stress.

Also, the antioxidant for prevention or treatment of a brain disease comprising the *Petasites japonicus* extract as an effective ingredient may be used in combination with any antioxidant substance which is commonly used and *Petasites japonicus* of this invention.

BRIEF DESCRIPTION OF DRAWINGS

Further objects and advantages of the invention can be more fully understood from the following detailed description taken in conjunction with the accompanying drawings in which.

A: CA1 site of the normal hippocampus of a non-treated mouse.

B: CA3 site of the normal hippocampus of non-treated mouse.

C: CA1 site of the hippocampus of a IA-treated mouse.

D: CA3 site of the hippocampus of a KA-treated mouse.

E: CA1 site of the hippocampus of a mouse which has been treated with the butanol fraction of *Petasites japonicus* and then KA, F: CA3 site of the hippocampus of a mouse which has been treated with the butanol fraction of *Petasites japonicus* and then KA.

BEST MODE FOR CARRYING OUT THE INVENTION

Now, the present invention will be described in detail by the following examples.

However, the examples are only for illustration and the present invention is limited thereto.

EXAMPLE 1

Preparation of *Petasites japonicus* Extract

Figure 1:
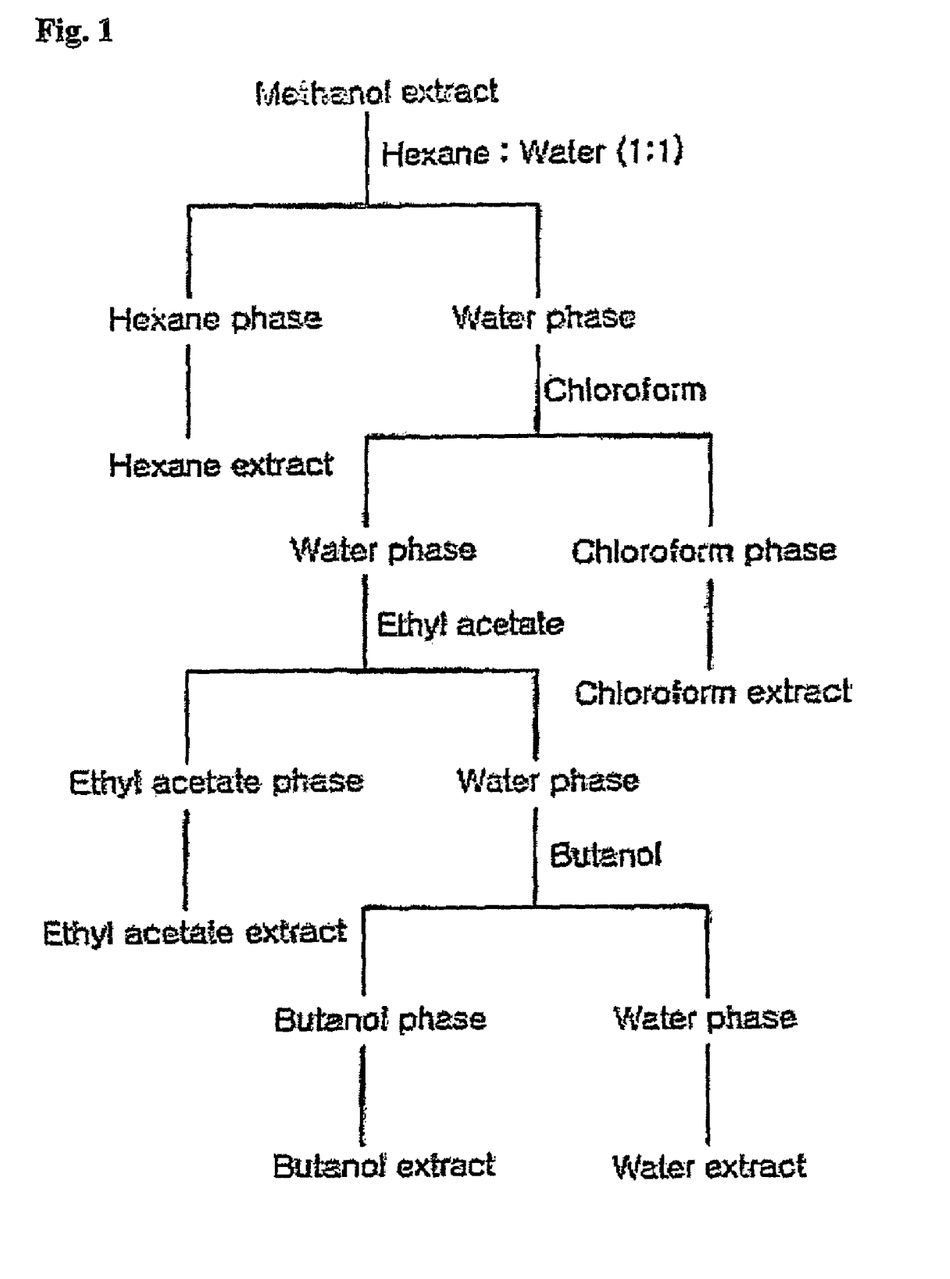
FIG. 1 is a schematic view showing the steps to fractionate the methanol extract of *Petasites japonicus* with various solvents.

Butterbur (*Petasites japonicus*) was dried in a dark place. Dried *Petasites japonicus* was ground. 500 g of dry *Petasites japonicus* was added to 5 l of 99.9% methanol and extracted 3 times in a dark room at 15° C. The resulting methanol extract of *Petasites japonicus* was concentrated in a rotary evaporator at 40° C. under reduced pressure to remove methanol and the residue was taken into distilled water. To the *Petasites japonicus* extract dissolved in distilled water, hexane in the same volume was added for phase separation and the hexane phase was removed. To the remaining water phase, ethyl acetate was added in the same volume for phase separation and the ethyl acetate phase was removed. To the remaining water phase after the ethyl acetate phase was removed off, butanol was added in the same volume for phase separation to obtain a butanol phase and a water phase. The resulting hexane phase, chloroform phase, ethyl acetate phase, butanol phase and water phase were separately evaporated under a low temperature and low pressure condition to obtain a hexane fraction, a methanol fraction, an ethyl acetate fraction, a butanol fraction and a water fraction (FIG. 1).

EXAMPLE 2

Assay of Antioxidant Activity of *Petasites japonicus* Methanol Extract

In order to examine whether the *Petasites japonicus* extract according to the present invention has antioxidant activity, the extracts of *Petasites japonicus* with various solvents obtained from Example 1 was subjected to an in vitro experiment comprising treating the brain of a mouse with each f the extracts and measuring lipid peroxidation. Concretely, the brain of an ICR male mouse (22.5±2.5 g, 6 to 8 weeks old) was removed and washed with 0.15 M KCl solution containing 2 mm EDTA. The washed brain was ground using a tissue homogenizer (Teflon pestle). To 1 ml of the ground brain, 1 ml of 8.1% SDS, 2 ml of 20% acetic acid and 1 ml of 0.75% thiobarbituric acid (TBA) were added. The resulting mixture was boiled, cooled in ice for 30 minutes and centrifuged at 14,000 rpm for 10 minutes to obtain the supernatant. To the supernatant, 1 ml of each of the various solvent fractions of *Petasites japonicus* from Example 1 was added and $Fe^{2+}$ 0.2 mM and ascorbic acid 25 mM were added. The resulting mixture was thoroughly mixed while stirring at 37° C. After 30 minutes, to the mixture, 15% trichloroacetic acid (TCA) and 0.75% TBA were added in the same volume as the mixture. The reaction was boiled for 15 minutes, stored in ice for 5 minutes and centrifuged at 3,000 rpm for 10 minutes to remove corpuscolates. The supernatant was taken and measured for absorption at 533 nm (Bidlack, W. T., and Tappel, A. L., *Lipids*, 1973, 8, 177-182). Malondialdehyde (Gutteridge, J. M. C., *Analytical Biochemistry*, 1975, 69, 518-526) produced by hydrolysis of 1,1,3,3,-tetraethoxypropane) was used for calibration. The inhibition of lipid peroxidation was shown by log concentration exhibiting 50% inhibitory effect as median effective concentration ($IC_{50}$) from a curve showing inhibition of lipid peroxidation when the extract was treated at 8 concentrations. The antioxidant activity Was shown by reduction (%) of thiobarbituric acid reactive substrate (TBARS) over control (without treatment), as shown in Equation 1.

antioxidant activity (%)=[1−($A_{sample}$−$A_{reference1}$)/($A_{reference2}$−$A_{control}$)]×100     <Equation 1>

$A_{sample}$: absorption of a mixture of brain hydrogenate, ascorbic acid/$Fe^{2+}$ and *Petasites japonicus* extract at 533 nm, $A_{reference1}$: absorption of a mixture of brain hydrogenate and *Petasites japonicus* extract at 533 nm, $A_{reference2}$: absorption of a mixture of brain hydrogenate and ascorbic acid/$Fe^{2+}$ at 533 nm, $A_{control}$: absorption of brain hydrogenate at 533 nm.

As a result, among the solvent fractions obtained from the methanol extract of *Petasites japonicus*, the ethyl acetate and butanol fractions showed the lowest $IC_{50}$ value (Table 1). Therefore, it was noted that the ethyl acetate fraction which had been prepared by further extracting the methanol extract of *Petasites japonicus* with ethyl acetate and the butanol fraction which had been prepared by further extracting the methanol extract of *Petasites japonicus* with butanol had excellent lipid peroxidation inhibitory activity, that is, antioxidant activity.

TABLE 1

| *Petasites japonicus* fractions | $IC_{50}$ (mg/ml) |
| --- | --- |
| Ethyl acetate | 0.020 |
| chloroform phase | 0.245 |
| Butanol | 0.023 |
| Water | 0.117 |
| Ascorbic acid (control) | 0.790 |

EXAMPLE 3

Inhibition of Oxidative Neurotoxicity Induced by Kainic Acid

In order to examine the effect of the butanol fraction of *Petasites japonicus* which had been proved to have excellent antioxidant activity in Example 2 on neurotoxicity, an in vivo experiment was performed to analyze the effect on oxidative neurotoxicity induced by kainic acid (KA).

<3-1> Assay of Fatality Rate, Body Weight, Neurotoxicity by Administration of Butanol Fraction of *Petasites japonicus*

Male ICR mice (22.5±2.5 g, 6 to 8 weeks old) were freely fed with solid feed for experimental animals (SamYang Co. Korea) in a polycarbonate cage (5 animals per cage). The mice were bred under conditions including a temperature and a relative humidity maintained at 23±3° C. and 60±10%, respectively, a light-dark cycle of 12 hours and illumination of 150 to 200 Lux. Only the animals which had been judged to be healthy during the acclimation period were randomly assigned to groups for the experiment. The breeding and experiment of animals were performed according to Guide for care and use of laboratory animal (National Institutes of Health Guidelines, 1985, 85-23). The groups of mice were unspecifically grouped and the body weight was measured every day. The mice were orally injected with the butanol fraction of *Petasites japonicus* extracted in Example 1 in an amount of 150 or 400 mg/kg once per day for 4 days using an esophagus needle. On the next day after the injection of the butanol fraction of *Petasites japonicus*, KA dissolved in saline was intraperitoneally injected to mice in an amount of 50 mg per 1 kg of body weight. Control mice were injected with saline instead of the butanol fraction. After the KA injection, the behavioral change of the mice was monitored by the method of Kondo et al. (*Journal of Cerebral Blood Flow and Metabolism*, 1997, 17, 241-256). Also, on the next day after the KA injection, the brains were removed from the mice, frozen in liquid nitrogen and stored at −80° C. for 48 hours at maximum until used.

1. Fatality Rate

KA, and KA and the butanol fraction of *Petasites japonicus* were administered and the fatality rate was measured. As a result, the mice administered with the butanol fraction of *Petasites japonicus* prior to KA showed lower fatality rate, as compared to the animals administered with only KA, and the animals administered at 150 mg/kg showed higher fatality, as compared to the animals administered at 400 mg/kg (Table 2). Therefore, it was noted that the butanol fraction of *Petasites japonicus* concentration-dependently reduced the KA-induced fatality rate of mice.

TABLE 2

| Groups | | Fatality rate (%) |
| --- | --- | --- |
| Exp. Group 1 | Control | 0 |
| | KA (50 mg/kg) | 54 |
| | KA (50 mg/kg) + butanol fraction *Petasites japonicus* (400 mg/kg) | 25 |
| Exp. Group 2 | Control | 0 |
| | KA (50 mg/kg) | 63.6 |
| | KA (50 mg/kg) + butanol fraction *Petasites japonicus* (150 mg/kg) | 50 |

However, as can be seen from Table 2, even when the butanol fraction of *Petasites japonicus* was administered in an amount of 150 mg/kg, the fatality rate was as high as 50%. Therefore, the butanol fraction of *Petasites japonicus* was mixed with a 10 times volume of butanol to obtain a fraction being less soluble in butanol and a fraction being more soluble in butanol, which are assigned to Fraction I and Fraction II, respectively. The fractions were subjected to the same procedures as described above to measure the fatality rate.

As result, when the Fraction I was administered, the fatality rate was found to be 0%. The Fraction II showed a fatality rate of 44%. Thus, it was noted that the fraction which had been further extracted with butanol had a low fatality rate (Table 3). It is believed that components contained in the fraction being less soluble in butanol are factors toxic to mice.

TABLE 3

| Groups | Fatality rate (%) |
| --- | --- |
| KA (44 mg/kg) | 54 |
| KA (44 mg/kg) + fraction I (200 mg/kg) | 0 |
| KA (44 mg/kg) + fraction II (200 mg/kg) | 44.4 |

2. Change in Body Weight and Brain Weight

After the *Petasites japonicus* butanol fraction was administered in an amount of 400 mg/kg, the mice were measured for body weight and brain weight. As a result, the administration of the butanol fraction of *Petasites japonicus* did not affect the body weight and brain weight (Table 4). Also, even when the Fraction I or Fraction II was administered in an amount of 200 mg/kg, the body weight and brain weight were not affected. Particularly, the Fraction I less affected the body weight and brain weight than the Fraction II (Table 5). Therefore, it was noted that the *Petasites japonicus* methanol extract according to the present invention did not show side effects even when directly administered.

TABLE 4

| Groups | Initial body weight (g) | Final body weight (g) | Body weight change (g) | Brain weight (g) |
|---|---|---|---|---|
| Control | 31.48 ± 1.09 | 32.06 ± 1.06 | 0.58 ± 0.008 | 0.355 ± 0.0059 |
| KA (50 mg/kg) | 31.39 ± 0.49 | 32.34 ± 0.58 | 0.95 ± 0.385 | 0.346 ± 0.0038 |
| KA (50 mg/kg) + Petasites japonic butanol fraction (400 mg/kg) | 31.71 ± 0.7 | 33.21 ± 0.74 | 1.51 ± 0.247 | 0.353 ± 0.0066 |

TABLE 5

| Groups | Initial body weight (g) | Final body weight (g) | Body weight change (g) | Brain weight (g) |
|---|---|---|---|---|
| Control | 30.04 ± 0.71 | 30.09 ± 0.95 | 0.05 ± 0.51 | 0.304 ± 0.0059 |
| KA (44 mg/kg) | 29.49 ± 0.91 | 29.88 ± 0.86 | 0.39 ± 0.29 | 0.327 ± 0.0098 |
| KA (44 mg/kg) + fraction I (200 mg/kg) | 31.66 ± 0.65 | 31.49 ± 0.74 | 0.18 ± 0.39 | 0.328 ± 0.0178 |
| KA (44 mg/kg) + fraction II (200 mg/kg) | 30.56 ± 0.88 | 29.33 ± 1.16 | 1.12 ± 0.54 | 0.319 ± 0.0051 |

3. Neuronal Behavior Change

Mice were administered with Fraction I or Fraction II of *Petasites japonicus* in an amount of 200 mg/kg and observed for neuronal behavior change (1 stage; tail arch, 2 stage; tremor, 3 stage; seizure). As a result, the *Petasites japonicus* Fraction I maintained tail arch but reduced tremor and seizure to 77.8% and 66.7%, respectively, as compared to the mice administered with on KA. The *Petasites japonicus* fraction II showed the neuronal behavior change more rapidly than the Fraction I. It is believed that this is because the components contained in the fraction being less soluble in butanol were toxic to the animal (Table 6). Therefore, it was noted that the butanol fraction of *Petasites japonicus* could relieve the neurotoxic behavior induced by KA.

TABLE 6

| Groups | Tail arch | Tremor | Seizure |
|---|---|---|---|
| KA (44 mg/kg) | 12.4 ± 4.7 (100%) | 16.7 ± 6.1 (100%) | 18.9 ± 19.5 (100%) |
| KA (44 mg/kg) + fraction I (200 mg/kg) | 27.6 ± 7.6 (100%) | 40.6 ± 11.9 (77.8%) | 48.2 ± 10.4 (66.7%) |
| KA (44 mg/kg) + fraction II (200 mg/kg) | 11.4 ± 7.6 (100%) | 17.0 ± 9.7 (100%) | 22.6 ± 16.8 (88.9) |

Figure 2:
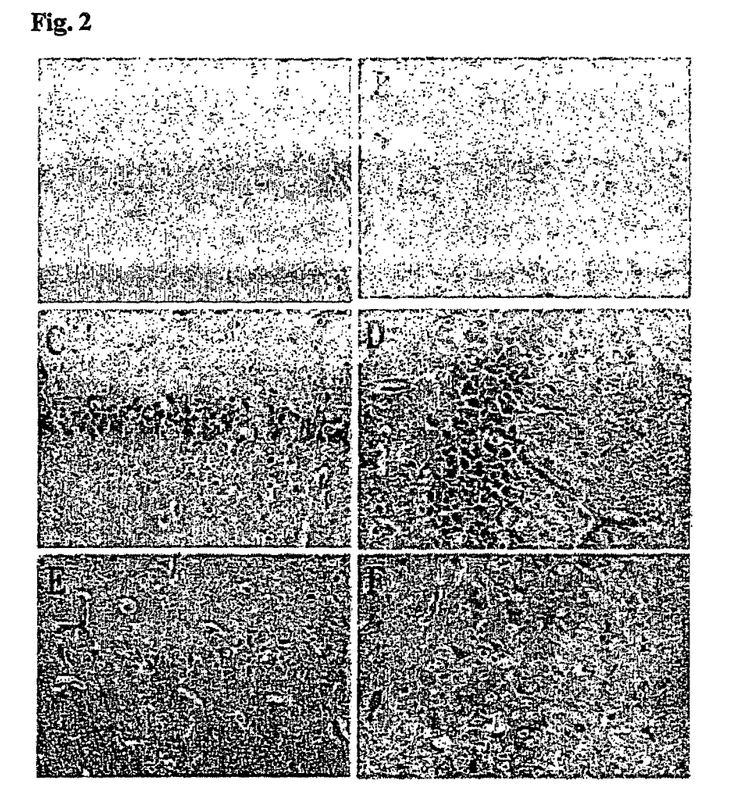
FIG. 2 is a photograph showing the effect on survival of hippocampus nerve cells induced by KA when the butanol fraction of *Petasites japonicus* is administered to mice.
Figure 3A:
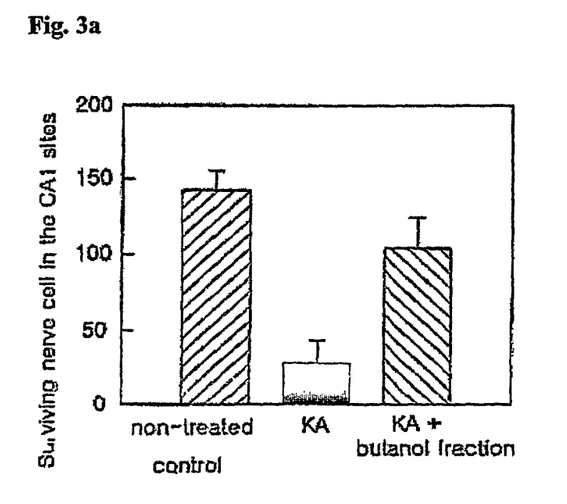
FIG. 3a is a graph constructed by counting the number of surviving cells to show the effect on the survival of nerve cells existing in the CA1 site of the hippocampus induced by KA when the butanol fraction of *Petasites japonicus* is administered to mice.
Figure 3B:
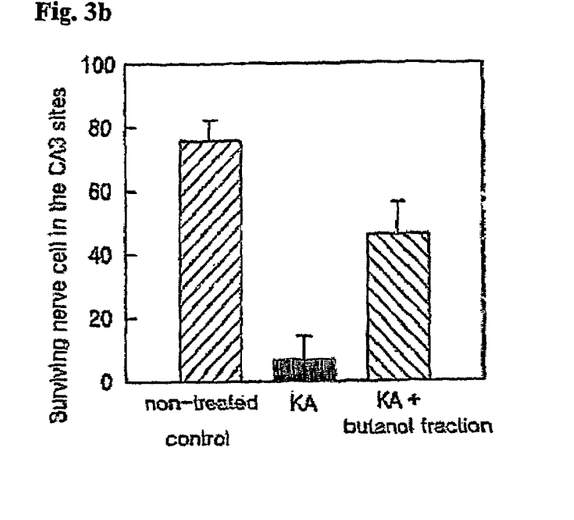
FIG. 3b is a graph constructed by counting the number of surviving cells to show the effect on the survival of nerve cells existing in the CA3 site of the hippocampus induced by KA when the butanol fraction of *Petasites japonicus* is administered to mice.

Also, the brain removed on the next day after the administration of KA was subjected to a tissue biopsy to examine damage of pyramidal cells in CA1 and CA3 sites of the hippocampus. As a result, the surviving nerve cells in the CA1 and CA3 sites of the hippocampus after the administration of KA were 18.5% and 8.9%, respectively, which indicated that almost nerve cells were damaged. However, when the butanol fraction of *Petasites japonicus* was pre-treated, the surviving nerve cells were 72.6% and 62.2%, respectively, and thus, it was noted that the fraction had neuroprotective effect (FIG. 2, FIG. 3a and FIG. 3b).

<3-2> Analysis of Antioxidant Substance by Administration of Butanol Fraction of *Petasites japonicus*

The brains were removed from mice which had been administered with only KA and mice which had been administered with 400 mg/kg of the *Petasites japonicus* butanol fraction. About 0.2 g of brain tissue from each brain was put into cold 6% metaphosphoric acid solution and crushed using a cold ceramic percussion motor. The crushed solution was centrifuged at 4° C., 27,000 g for 20 minutes. The supernatant was taken. To 0.05 Ml of the supernatant, 0.39 Ml of 100 mM phosphate buffer (pH 7.4) containing 5 mM EDTA, 0.025 ml of 10 mM DTNB (5,5-dithiobis-(2-nitrobenzoic acid)) and 0.08 ml of 5 mM NADPH were added and equilibrated at 25° C. for 3 minutes. Then, 2 units of glutathione (GSH) reductase was added thereto to initiate a reaction. The formation of 2-nitro-5-thiobenzoic acid was monitored by measuring the adsorption at 412 nm using a UV/VIS spectrophotometer (Roberts, J. C. and Francetic, D. J., *Analytical Biochemistry*, 1993, 211, 183-187; Raymond, C. et al., *Journal of Nutrition*, 1995, 125, 3062-3070). The total GSH amount contained in a sample was determined from a standard curve constructed by plotting the adsorption at 412 nm versus the known amount of GSH. The amount of GSH was shown by an average±S.E.M of data obtained by performing the experiment using 4 to 8 mice 3 times.

Figure 4:
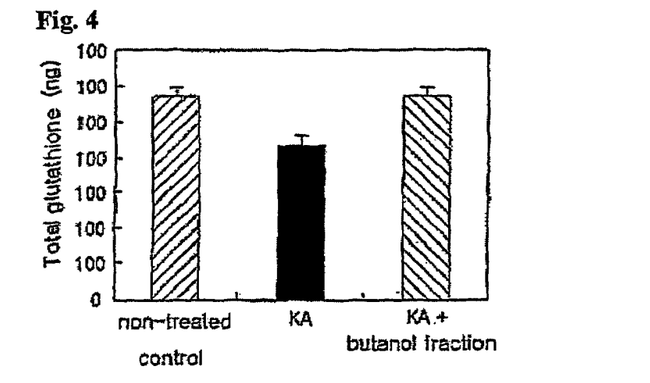
FIG. 4 is a graph showing the effect on reduction in the amount of glutathione induced by KA when the butanol fraction of *Petasites japonicus* is administered to mice.

As a result, when KA was administered alone, the total GSH amount in the brain tissue was significantly reduced to 20%. When the butanol fraction of *Petasites japonicus* was administered in an amount of 400 mg/kg prior to KA, the GSH amount was recovered to a level of the non-treated control (FIG. 4). Therefore, it was noted that the butanol fraction of *Petasites japonicus* according to the present invention has antioxidant effect.

<3-3> Assay of Lipid Peroxidation by Administration of *Petasites japonicus* Butanol Fraction Since KA induces lipid peroxidation, this example was performed to examine the effect of the butanol fraction of *Petasites japonicus* according to the present invention on the KA-induced lipid peroxidation in mice. Concretely, the brains were removed from mice The brains were removed from mice which had been administered with only KA and mice which had been administered with 400 mg/kg of the *Petasites japonicus* butanol fraction. Brain tissue from each brain was crushed in 0.25M sucrose solution and the crushed brain homogenate was measured for the TBARS amount contained therein.

Figure 5:
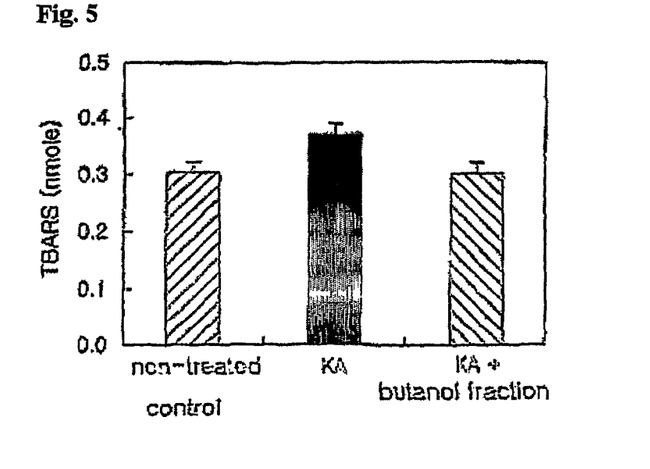
FIG. 5 is a graph showing the inhibiting effect on the lipid peroxidation induced by KA when the butanol fraction of *Petasites japonicus* is administered to mice.
Figure 6A:
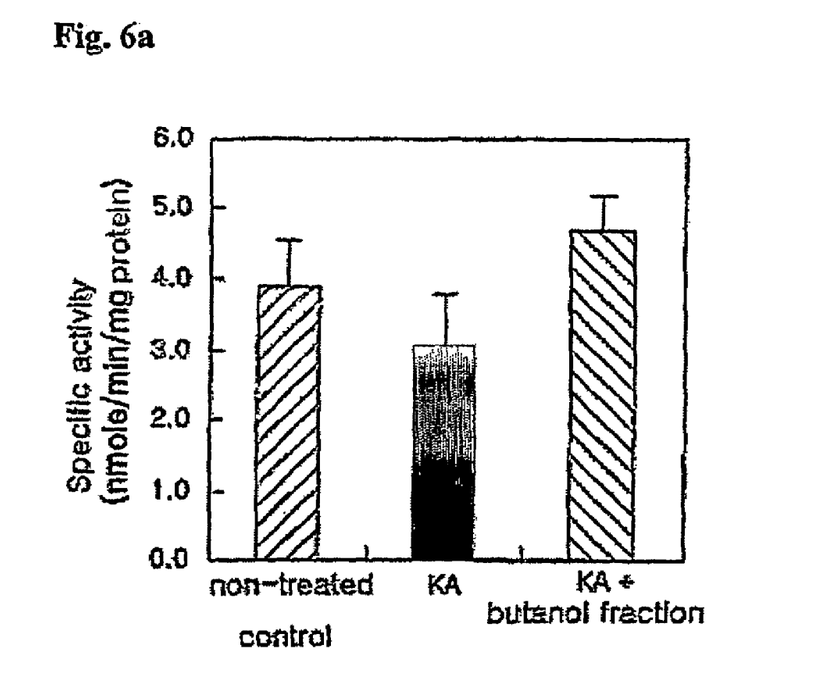
FIG. 6a is a graph showing the effect on the reduction in glutathione peroxidase activity induced by KA when the butanol fraction of *Petasites japonicus* is administered to mice.

As a result, the TBARS content increased by addition of KA alone was returned to a level of the non-treated control by pre-treatment of the butanol fraction of *Petasites japonicus* according to the present invention (FIG. 5). Also, the Fraction I and Fraction II of *Petasites japonicus* showed the same results as above. Therefore, it was noted that the butanol fraction of *Petasites japonicus* according to the present invention can prevent lipid peroxidation by oxidative stress in brain tissue.

<3-4> Assay of Antioxidant Enzyme Activity by Administration of Butanol Fraction of *Petasites japonicus*

This example was performed to identify the antioxidant effect the butanol fraction of *Petasites japonicus* according to the present invention to inhibit peroxidation induced by KA and the mechanism of the effect on the antioxidation-related enzyme activity. Concretely, the brain homogenate obtained from Example <3-3> was used to measure activities of glutathione-related antioxidant enzymes, that is, glutathione peroxidase and glutathione reductase.

Figure 6B:
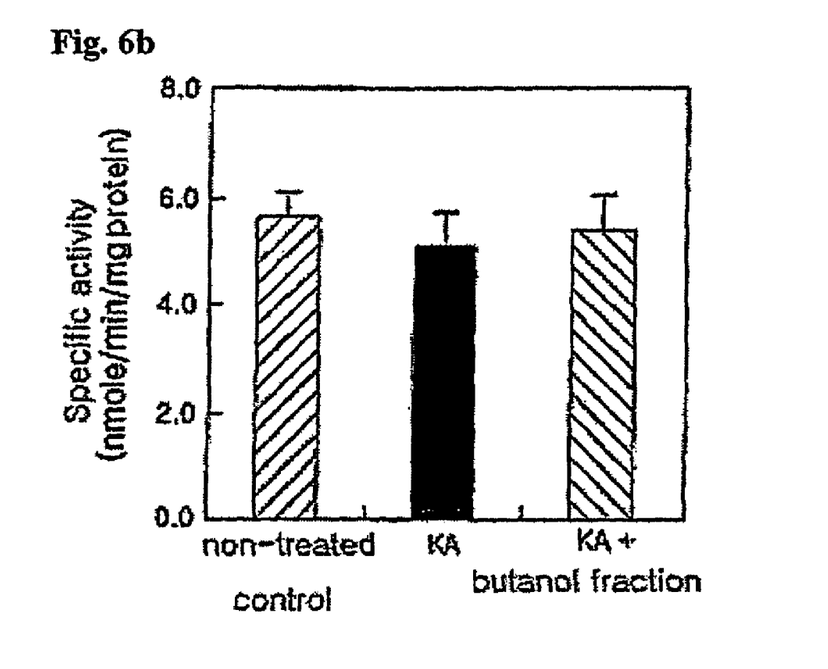
FIG. 6b is a graph showing the effect on the reduction in glutathione reductase activity induced by KA when the butanol fraction of *Petasites japonicus* is administered to mice.

As a result, the glutathione peroxidase activity reduced by KA was significantly increased to a level higher than the non-treated control by pre-administering the butanol fraction of *Petasites japonicus* according to the present invention (p<0.05) (FIG. 6a). On the other hand, the butanol fraction of *Petasites japonicus* according to the present invention did not affect the activity of glutathione peroxidase activity reduced by KA (FIG. 6b).

Also, the butanol fraction of *Petasites japonicus* was again dissolved in butanol and the non-dissolved phase was removed. The dissolved phase was administered to mice and measured for fatality rate, body weight change, brain weight change, neurotoxic behavior change, tissue observation of nerve cells, analysis of glutathione content, analysis of expression of glutathione reductase and glutathione peroxidase.

As a result, the fraction obtained by re-extraction of the butanol fraction of *Petasites japonicus* showed the same result as the results of the butanol fraction of *Petasites japonicus*.

As described above, it was noted that the *Petasites japonicus* extract according to the present invention had excellent antioxidant activity, inhibitory effect of lipid peroxidation and thus, could be usefully used in the prevention and treatment of brain diseases induced by peroxidation.

Now, the concrete diseases which can be prevented or treated by using the *Petasites japonicus* extract according to the present invention will be described.

<Application 1> Alzheimer's Disease (AD)

Alzheimer's disease accompanies with necrosis of glutamatergic neurons in the cerebral cortex and hippocampus and cholinergic neurons in the forebrain base and exhibits common phenomena of amyloid plaque outside of neurons and neurofibrillary tangles in neurons. Also, it is known that by an excessive amount of reactive oxygen, lipid peroxidation, 8-hydroxy deoxyguanosine, protein carbonyls, nitration, oxidative crosslinking of proteins and the like are increased in Alzheimer's disease (Vitek et al., 1994, *Proc. Natl. Acad. Sci. U.S.A.*, 91, 4766-4770; Smith et al., 1995, *Trends. Neurosci.*, 18, 172-176; Smith et al., 1996, *Mol. Chem. neuropathol.*, 28, 41-48, Smith et al., 1997, *Proc. Natl. Acad. Sci. U.S.A.*, 94, 9866-9868; Montine et al., 1996, *J. Neuropathol. Exp. Neurol.*, 55, 202-201). Therefore, the extract according to the present invention having excellent lipid peroxidation inhibitory activity and antioxidation-related enzyme activity can be usefully used in the treatment and prevention of Alzhemier's disease.

<Application 2> Parkinson's Disease

Parkinson's disease is one of neurodegenerative diseases which accompanies with necrosis of dopamine neurons existing in the substanitia nigra and exhibits various symptoms such as tremor, muscular stiffness, bradykinesia, abnormal posture, akinesia and the like. As one of the main causes of neuron necrosis, the oxidative toxins have been proposed, which include increases of lipid peroxidation, DNA oxidation, protein carbonyl and nitrotyrosine in the substanitia nigra (Bowling, A. C. and Beal, M. F., *Life Sci.*, 1995, 56(14), 1151-1171). Therefore, the extract according to the present invention having excellent lipid peroxidation inhibitory activity and antioxidation-related enzyme activity can be usefully used in the treatment and prevention of Parkinson's disease.

<Application 3> Lou Gehrig's Disease (Amyotrophic Lateral Sclerosis)

Amyotrophic lateral sclerosis accompanies damage of motor neurons of cerebral cortex, brain stem, spinal cord, beginning with lower motor neurons of the spinal nerve and gradually progressing along upper motor neurons, and exhibits characteristic amyotrophy, weakness of breathing strength and fasciculation. The patients generally die in 2 to 5 years from the first observation of the symptoms. Particularly, it has been reported that hereditary Amyotrophic lateral sclerosis patients have a mutation in SOD-1 gene to remove superoxide radical existing on chromosome 21, causing oxidative toxicity and protein carbonyl, which is an index of oxidative toxicity, is increased in the brain of the patients (Bowling et al., 1993, *J. Neurochem.*, 61, 2322-2325). Therefore, the extract according to the present invention having excellent lipid peroxidation inhibitory activity and antioxidation-related enzyme activity can be usefully used in the treatment and prevention of amyotrophic lateral sclerosis.

<Application 4> Hypoxic-ischemic Injury

Hypoxic-ischemic injury is a disease induced by lack of dextrose and oxygen supplied in a regular amount by blood circulation disorders in the brain (thrombosis, embolism, stenosis) and exhibits paralysis, language and cognitive dysfunction due to control loss of body functions by the damaged brain. After development of hypoxic-ischemic injury, calcium is introduced into cells by membrane depolarization and then into mitochondria, which causes damage of respiratory chain and increase in production of reactive oxygen, thereby accumulating excessive amount of reactive oxygen in cells. The produced reactive oxygen induces destruction of cellular membrane lipid, damage of genes, protein denaturation and the like, thereby causing neuron necrosis. An antioxidant has the effect of inhibiting ischemic neuron necrosis (Holtzman et al., 1996, *Ann. Neurol.*, 39(1), 114-122; Ferrer et al., 2001, *Acta neuropathol. (Berl.)*, 101(3), 229-38; Hall et al., 1990, *Stroke*, 21, 11183-11187). Therefore, the extract according to the present invention having excellent lipid peroxidation inhibitory activity and antioxidation-related enzyme activity can be usefully used in the treatment and prevention of hypoxic-ischemic injury.

<Application 5> Chronic Spinal Cord Injury

Chronic spinal cord injury causes paraparesis and quadriplegia and shows neuron necrosis to a site remote from the damaged part. However, a therapeutic agent or method for this disease has not yet developed. It has been reported that spinal cord injury shows introduction of $Ca^{2+}$, collapse of cellular membrane, lipid peroxidation by oxidative toxicity (Brown and Hall, 1992, *J. Am. Vet. Med. Assoc.*, 200, 1849-1859; Springer et al., 1997, *J. Neurochem.*, 68, 2469-2476; Juurlink and Paterson, 1998, *J. Spinal cord Med.*, 21, 309-334), and recently, evidences showing that necrocytosis is involved in secondary injury have been proposed. Also, it has been reported that an inhibitor of caspase which is an enzyme involved in necrocytosis reduces neuron necrosis (Zhang et al., 1990, *J. Neurochem.*, 59, 733-739). Therefore, the extract according to the present invention having excellent lipid peroxidation inhibitory activity and antioxidation-related enzyme activity can be usefully used in the treatment and prevention of chronic spinal cord injury.

INDUSTRIAL APPLICABILITY

As described above, the *Petasites japonicus* extract according to the present invention has excellent inhibitory activity on neurotoxicity in the brain by oxidative stress and lipid peroxidation and can be usefully used in the prevention and treatment of brain diseases induced by oxidative stress.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An extract of *Petasites japonicus* having antioxidant activity and therapeutic activity for a brain disease produced by the steps of:
   1) extracting and concentrating *Petasites japonicus* with an alcohol to obtain an alcohol extract;
   2) fractionating the alcohol extract from the step 1) with hexane and water into a hexane phase and a water phase and separating the water phase;
   3) fractionating the water phase from the step 2) with chloroform into a chloroform phase and a water phase and separating the water phase;
   4) fractionating the water phase from the step 3) with ethyl acetate into an ethyl acetate phase and a water phase and separating the water phase;
   5) fractionating the water phase from the step 4) with butanol into a butanol phase and a water phase and separating the butanol phase; and
   6) vaporizing the butanol phase from the step 5) at a low temperature and a low pressure to purify the butanol phase, or adding butanol to the butanol phase from the step 5) to obtain an extract that comprises a butanol-soluble phase having antioxidant activity.

2. The extract of *petasites japonicus* having antioxidant activity according to claim 1, in which the alcohol is methanol or ethanol.

3. The extract of *petasites japonicus* according to claim 2, in which the methanol is 95 to 100%.

4. An antioxidant composition for the treatment of a brain disease comprising the extract of *petasites japonicus* having antioxidant activity according to claim 1 as an effective ingredient.

5. The antioxidant composition according to claim 4, in which the brain disease is selected from the group consisting of Alzheimer's disease, Parkinson's disease, amyotrophic lateral sclerosis, hypoxic-ischemic injury and chronic spinal cord injury.

* * * * *